(12) United States Patent
Taniguchi et al.

(10) Patent No.: US 8,970,836 B2
(45) Date of Patent: Mar. 3, 2015

(54) DEFECT INSPECTING APPARATUS AND DEFECT INSPECTING METHOD

(75) Inventors: Atsushi Taniguchi, Tokyo (JP); Taketo Ueno, Tokyo (JP); Shunichi Matsumoto, Tokyo (JP); Yukihiro Shibata, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/235,916

(22) PCT Filed: May 14, 2012

(86) PCT No.: PCT/JP2012/003118
§ 371 (c)(1),
(2), (4) Date: Apr. 30, 2014

(87) PCT Pub. No.: WO2013/018255
PCT Pub. Date: Feb. 7, 2013

(65) Prior Publication Data
US 2014/0233024 A1    Aug. 21, 2014

(30) Foreign Application Priority Data
Jul. 29, 2011   (JP) ................. 2011-166200

(51) Int. Cl.
| G01N 21/00 | (2006.01) |
| G01N 21/95 | (2006.01) |
| G01N 21/956 | (2006.01) |
| G01N 21/21 | (2006.01) |
| G01N 21/88 | (2006.01) |
| G01B 11/06 | (2006.01) |

(52) U.S. Cl.
CPC ............ *G01N 21/95* (2013.01); *G01N 21/9501* (2013.01); *G01N 21/95607* (2013.01); *G01N 2021/9513* (2013.01); *G01N 21/211* (2013.01);
(Continued)

(58) Field of Classification Search
CPC . G01N 21/9501; G01N 21/94; G01N 21/956; G01N 2021/8822; G01N 21/47; G01N 21/8806; G01N 21/4738; G01N 21/00; G01N 2015/1486; G01N 2015/1493; G01N 21/93; G01N 21/95607; G01N 2021/4711
See application file for complete search history.

(56) References Cited

U.S. PATENT DOCUMENTS

| 4,468,120 A | * | 8/1984 | Tanimoto et al. | .......... 356/239.8 |
| 4,776,693 A | * | 10/1988 | Imamura et al. | .......... 356/237.3 |

(Continued)

FOREIGN PATENT DOCUMENTS

| JP | 2002-333313 A | 11/2002 |
| JP | 2005-164429 A | 6/2005 |

(Continued)

OTHER PUBLICATIONS

International Search Report with English translation dated Sep. 4, 2012 (5 pages).

*Primary Examiner* — Michael P Stafira
(74) *Attorney, Agent, or Firm* — Crowell & Moring LLP

(57) ABSTRACT

An invention being applied is a defect detecting apparatus that has: an illuminating optical system with a laser light source for irradiating a sample on whose surface a pattern is formed with light; a detecting optical system with a sensor for detecting light generated from the sample illuminated by the illuminating optical system; and a signal processing unit that extracts a defect from an image based on the light detected by the detecting optical system, in which an amplification rate of the sensor is dynamically changed during a time when the light is detected by the detecting optical system.

19 Claims, 7 Drawing Sheets

(52) U.S. Cl.
CPC .. *G01N 21/95623* (2013.01); *G01N 2021/8822* (2013.01); *G01B 11/0641* (2013.01)
USPC ............... 356/237.2; 356/237.3; 356/237.4

(56) References Cited

U.S. PATENT DOCUMENTS

| | | | |
|---|---|---|---|
| 5,105,092 A | * | 4/1992 | Natsubori et al. ....... 250/559.06 |
| 6,617,603 B2 | | 9/2003 | Ishiguro et al. |
| 8,599,369 B2 | | 12/2013 | Urano et al. |
| 2002/0080345 A1 | * | 6/2002 | Ishiguro .................. 356/237.2 |
| 2002/0125449 A1 | | 9/2002 | Ishiguro et al. |
| 2008/0002194 A1 | | 1/2008 | Matsui |

FOREIGN PATENT DOCUMENTS

| | | |
|---|---|---|
| JP | 2008-8803 A | 1/2008 |
| JP | 2011-2314 A | 1/2011 |

* cited by examiner

DEFECT INSPECTING APPARATUS AND DEFECT INSPECTING METHOD

BACKGROUND

The present invention relates to a defect inspecting apparatus and a defect inspecting method for inspecting a semiconductor wafer and a liquid crystal substrate.

When manufacturing an LSI and a liquid crystal substrate, there are repeated patterns formed on an object to be processed (for example, a semiconductor wafer). In manufacture of such an LSI or liquid crystal substrate, if a foreign substance adheres to a surface of the object to be processed or a defect occurs, it will become a cause of a defect, such as bad insulation of wiring and a short circuit, for example. Here, as the circuit pattern becomes minute, it has become difficult to discriminate between a pattern formed on the object to be processed (a non-defect part) and a minute foreign substance and a defect. Here, the defect is a particle adhering on a sample that is the object to be processed, a crystal defect COP (Crystal Originated Particle), and scratch resulting from polishing.

There is U.S. Pat. No. 6,617,603 (patent document 1) as a background art of this technology. This patent gazette describes a method for detecting a defect (abstract) by imaging a picture at a scan position on a disk plate that has a characteristic such that a center in an arrangement direction of n amplification type light receiving elements (avalanche photodiodes) in a light receiving area formed thereby takes a peak value and an amount of received light gradually decreases to its both sides actually in contrast and by using a fact that a profile of an amount of received light varies depending on existence/absence of the defect.

SUMMARY

Due to miniaturization of an inspection object (for example, a semiconductor pattern), a size of a defect to be inspected has become microminimized and an intensity of scattered light from the defect decreases considerably. In detecting very small scattered light from this defect, an existing CCD (Charge Coupled Device) array sensor and a TDI (Time Delay Integration) array sensor are insufficient in sensitivity. Although in U.S. Pat. No. 6,617,603, an element such that amplification type sensors are arranged in an array form is used for improvement in sensitivity, it comes with the following problem. When a light quantity of the scattered light varies greatly depending on a portion of the inspection object, if the sensitivity is set to a bright section so that the sensor may not be saturated, the sensitivity of a dark section will fall increasingly.

Moreover, there is reflection of a lens etc., weak defect scattered light is buried in these reflected lights, and the sensitivity falls.

Explaining briefly an outline of a representative mode among modes of the invention disclosed by the present application, it goes as follows: (1) A defect inspecting apparatus that has: an illuminating optical system having a laser light source for irradiating light onto a sample on whose surface a pattern is formed; a detecting optical system having a sensor for detecting light generated from the sample illuminated by the illuminating optical system; and a signal processing unit that extracts a defect from an image based on the light detected by the detecting optical system, in which an amplification rate of the sensor is dynamically changed during a time when the light is detected by the detecting optical system.

According to the present invention, it is possible to provide the defect inspecting apparatus and the defect inspecting method that realize a high sensitivity defect detection accuracy.

DETAILED DESCRIPTION

Hereinafter, embodiments will be described using drawings.

First Embodiment

A first embodiment of an optical inspecting apparatus according to the present invention will be described using FIG. 1 to FIG. 15. Below, the dark field inspecting apparatus will be explained taking the inspection of a semiconductor wafer with the dark field inspecting apparatus as an example.

Figure 1:
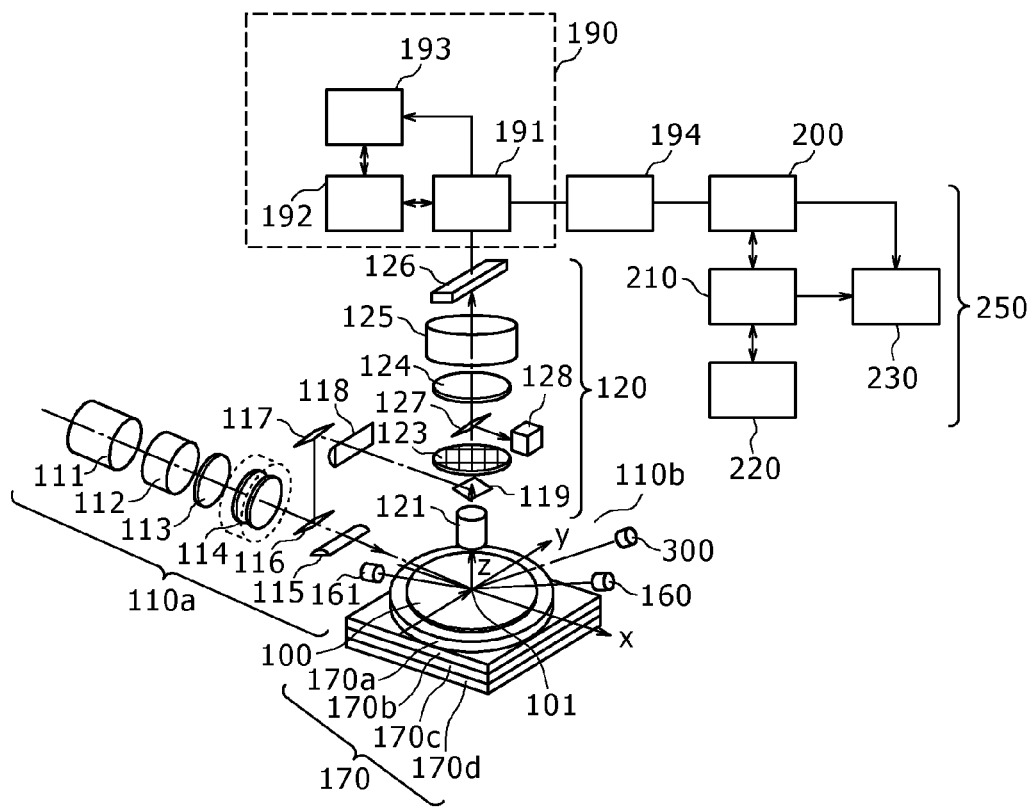
FIG. 1 is a block diagram showing an outline configuration of a first embodiment of an optical inspecting apparatus according to a first embodiment of the present invention.

FIG. 1 is a diagram showing the first embodiment of the optical inspecting apparatus according to the present invention. An illuminating optical system 110 illuminates a sample (semiconductor wafer) 100 that is an inspection object mounted on a stage part 170 with illumination light from a direction slanting relative to a normal direction of a surface of the semiconductor wafer 100 (oblique illumination), or illuminates it with a linear beam from the normal direction (epi-illumination), and detects scattered light that is scattered from the irradiated semiconductor wafer 100 with a detecting optical system 120. An array of APDs (Avalanche Photodiodes) whose amplification rate n is high and can be controlled at a high speed etc. is used to detect only the scattered light from the wafer in high sensitivity. In that occasion, the semiconductor wafer 100 that is mounted on the stage part 170 is scanned with the illumination light from an illuminating optical system 110a or 110b by driving the stage part 170 in a plane. A signal processing and control system 250 detects a defect existing on the semiconductor wafer 100 by processing the scattered light from the semiconductor wafer 100 detected by the detecting optical system 120.

[Oblique Illuminating Optical System 110a]

Figure 2:
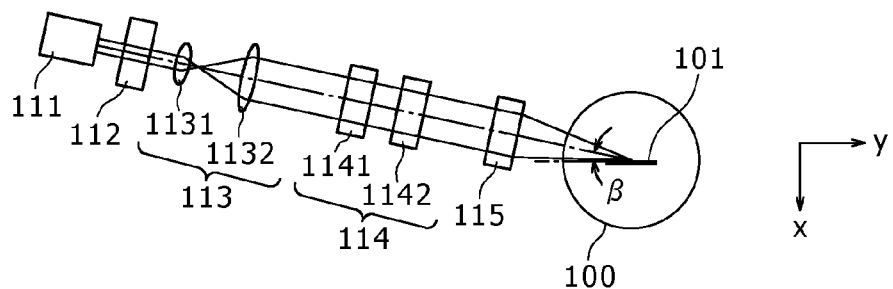
FIG. 2 is a plan view of an illuminating optical system of the optical inspecting apparatus according to the first embodiment of the present invention.
Figure 3:
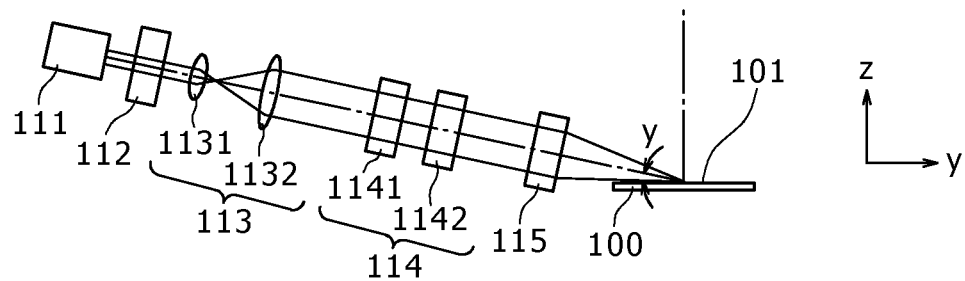
FIG. 3 is a side view of the illuminating optical system of the optical inspecting apparatus according to the first embodiment of the present invention.

The illuminating optical system 110a is comprised by having a laser light source 111, a light quantity adjustment unit (an attenuator, an ND (Neutral Density) filter) 112, a beam expander 113, a polarization generation part 114 comprised of a polarizer and a wave plate, a linear beam generation part (a linear illumination system) 115 for irradiating the inspection object (the semiconductor wafer) 100 with a linear beam. The laser light source 111 emits a laser beam. At this time, as the light source 111, a gas laser, a semiconductor laser, a solid state laser, a surface emitting laser, etc. are usable. Although regarding the wavelength of the light, lights in the infrared range, the visible range, and ultraviolet range can be used, since optical resolution improves as the wavelength becomes shorter, it is recommended to use light in the ultraviolet ranges such as UV (Ultra Violet), DUV (Deep Ultra Violet), VUV (Vacuum Ultra Violet), and EUV (Extreme Ultra Violet) lights in observing a minute defect. The beam shaping unit 113 shapes the laser beam emitted from the laser light source 111. FIG. 2 is a plan view of the illuminating optical system 110, and FIG. 3 is a side view thereof. In this embodiment, a beam shaping unit 113 is formed with a beam expander 1131 for enlarging a diameter of the laser beam emitted from the laser light source 111 and a collimating lens 1132 for forming an enlarged laser beam into collimated light. The polarization generation part 114 is comprised by having a polarizer 1141 and a wave plate 1142, and adjusts a polarization characteristic of the light whose beam diameter is enlarged by the beam expander 1131 of the beam shaping unit 113. The linear beam generation part 115 is comprised of a cylindrical lens etc.

In the above-mentioned configuration, the laser beam emitted from the laser light source 111 is adjusted in light quantity by the light quantity adjustment unit (attenuator, ND filter) 112, is expanded in beam diameter by the beam expander 1131 in the beam shaping unit 113, is formed into the collimated light by the collimating lens 1132, is controlled in polarization state by the polarization control part 114, and is focused into a one direction by the linear beam generation part 115 to become a linear beam 101 parallel to the y-axis, which is irradiated onto a linear area on the surface of the semiconductor wafer 100. At this time, illumination in an azimuth β with respect to the y-axis of the illuminating optical system shown in FIG. 2 can be realized by taking an arbitrary direction including the y-axis direction. Moreover, a polar angle γ that is an angle from the z-axis of the illuminating optical system shown in FIG. 3 is selected in a range of 0° to 90°. Incidentally, the illumination azimuth β and the polar angle γ are set not to interfere with the detecting optical system 120. At this time, the polarization generation part 114 may also be disposed after the linear beam generation part 115. The linear beam 101 thus formed is irradiated onto the surface of the semiconductor wafer 100 so that a stage y direction may coincide with a longitudinal direction of the linear beam 101.

[Epi-Illuminating Optical System 110b]

The epi-illuminating optical system 110b is comprised by having a branching mirror 116 for branching an optical path from the oblique illuminating optical system 110a, a mirror 117 for bending the optical path, a linear illuminating system (a linear beam generation part) 118, an illumination mirror 119 onto a wafer, and an objective lens 121 of the detecting optical system 120, and forms the linear beam 101 on the wafer. When using an oblique illuminating optical system 110a, the branching mirror 116 and the illumination mirror 119 are evacuated from the optical system. Although a disposition place of the branching mirror 116 may be in front of the beam shaping unit 113 and the polarization generation part 114, in that case, a polarization generation part and a beam formation unit become necessary for an epi-illuminating optical system.

Figure 4:
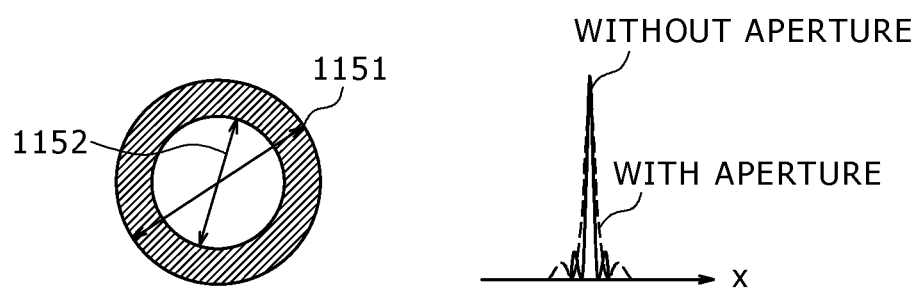
FIG. 4 is a diagram showing a thin line width adjustment mechanism of illumination according to the first embodiment of the present invention.
Figure 5:
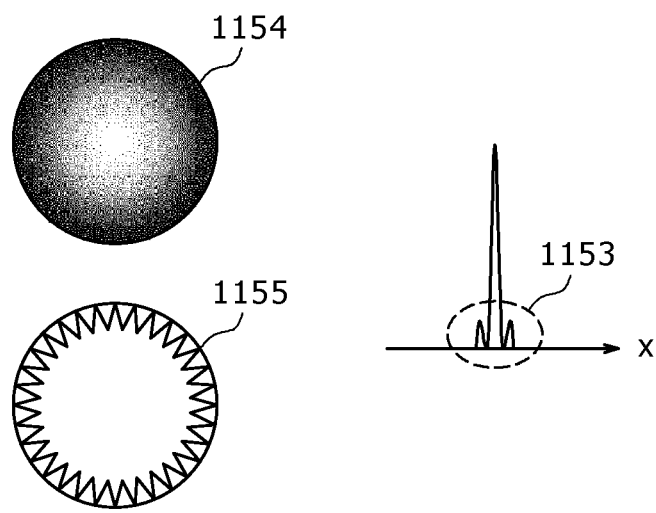
FIG. 5 is a diagram showing a side lobe inhibition mechanism of the illumination according to the first embodiment of the present invention.

Incidentally, in the optical system using linear illumination, a difference between the line width of the linear beam and side lobes becomes a difference of sample scattered light, which causes a difference of the detection sensitivity to occur. Since the line width and the side lobes have a relationship of the Fourier transform with pupil surfaces of the linear illuminating optical systems 115, 118, they can be controlled by a pupil surface shape. FIG. 4 is a diagram showing a thin line width adjustment mechanism of the illumination according to the first embodiment of the present invention, and FIG. 5 is a diagram showing a side lobe inhibition mechanism of the illumination according to the first embodiment of the present invention. As shown in FIG. 4, since the line width depends on an illumination NA, the line width can be controlled in a direction that makes the line width thick by controlling the pupil with an aperture 1152 whose diameter is smaller than a pupil diameter 1151. As shown in FIG. 5, side lobes 1153 can be reduced by varying the transmissivity from a boundary of the pupil inward toward its center continuously. Moreover, in order to obtain the same effect, there is also a technique of providing a minute structure that is decided by the pupil diameter and the wavelength in the pupil.

[Detecting Optical System 120]

The detecting optical system 120 will be explained in detail using FIG. 1. The detecting optical system 120 is comprised by having the objective lens 121, a spatial filter 123, an ellipsometer 124, an imaging lens 125, an amplifying sensor array 126, a beam sampler 127, and a pupil observation optical system 128. The pupil observation optical system 128 observes the pupil on an outgoing side of the objective lens 121. For leading the light to the pupil observation optical system 128, the light is led thereto from the detecting optical system 120 using the beam sampler 127 that can be taken into and out of an optical path of the detecting optical system 120. Incidentally, as a replacement for the pupil observation optical system 128, if it is possible that a relationship of a position and a shape of the spatial filter 123 with an intensity of an image acquired by the line sensor is obtained in advance and an intensity distribution at a pupil position is grasped from the relationship, the pupil observation optical system 128 for directly observing the pupil surface can be omitted. The objective lens 121 converges the reflected, scattered, and diffracted lights going in different directions from the surface of the semiconductor wafer 100. The spatial filter 123 shields a part of reflected, scattered, and diffracted lights from the surface of the semiconductor wafer 100 that are converged by the objective lens 121. Here, the spatial filter 123 is disposed at a position of the outgoing side pupil position of the objective lens 121 or at a position equivalent (conjugate) to the pupil position. As the spatial filter 123, a light shielding filter comprised of multiple rods having multiple thicknesses that can be arranged in vertical and horizontal directions, a filter that can allow light to pass or shield it at desired places two-dimensionally at the pupil surface, or the like is used. Especially, as the two-dimensional filter, one that uses an electrooptical effect such as a liquid crystal, one that uses a magnetooptical effect, a MEMS (Micro Electro Mechanical Systems) shutter, etc. are used. Incidentally, in this embodiment, in order that the illumination light is made into a linear shape with the y direction coinciding with the longitudinal direction, the light is focused in the y direction by the linear beam generation part 115. Therefore, a diffraction pattern on the pupil surface becomes a diffraction pattern that has a spreading in the y direction that depends on a focusing NA. In this case, the diffracted light is appropriately removable with a rod like filter disposed in a one direction.

The ellipsometer 124 is comprised by having the polarizer and the wave plate, and adjusts the polarization characteristic of the scattered light that was not shielded by the spatial filter 123. The polarization generation part 124 is comprised, for example, by having a ¼ wave plate, a ½ wave plate, and the polarizer, and each of these elements is controllable in rotation individually, which enables an arbitrary polarized light to be transmitted therethrough.

The imaging lens 125 makes the scattered light that was not shielded by the spatial filter 124 be transmitted, and images an optical image. Here, positions of the polarization analysis part spatial filter 124 and the imaging lens 125 may be interchanged.

The amplifying sensor array 126 is disposed at a position such that an image of the scattered light that is focused and imaged by the imaging lens 125 is imaged on a detection plane of the amplifying sensor array 126, and detects an optical image of the scattered light. As the amplifying sensor array 126, an APD (Avalanche Photodiode) array whose amplification rate can be varied at a high speed for every pixel by a voltage and whose sensor ON/OFF can be controlled at a high speed with an electrical signal, or the like is used. Since the amplification rate of the APD array varies depending on temperature, a voltage added with a temperature correction of a temperature monitor part 193 is applied to an amplifier 191 by a voltage controller 192.

Figure 6:
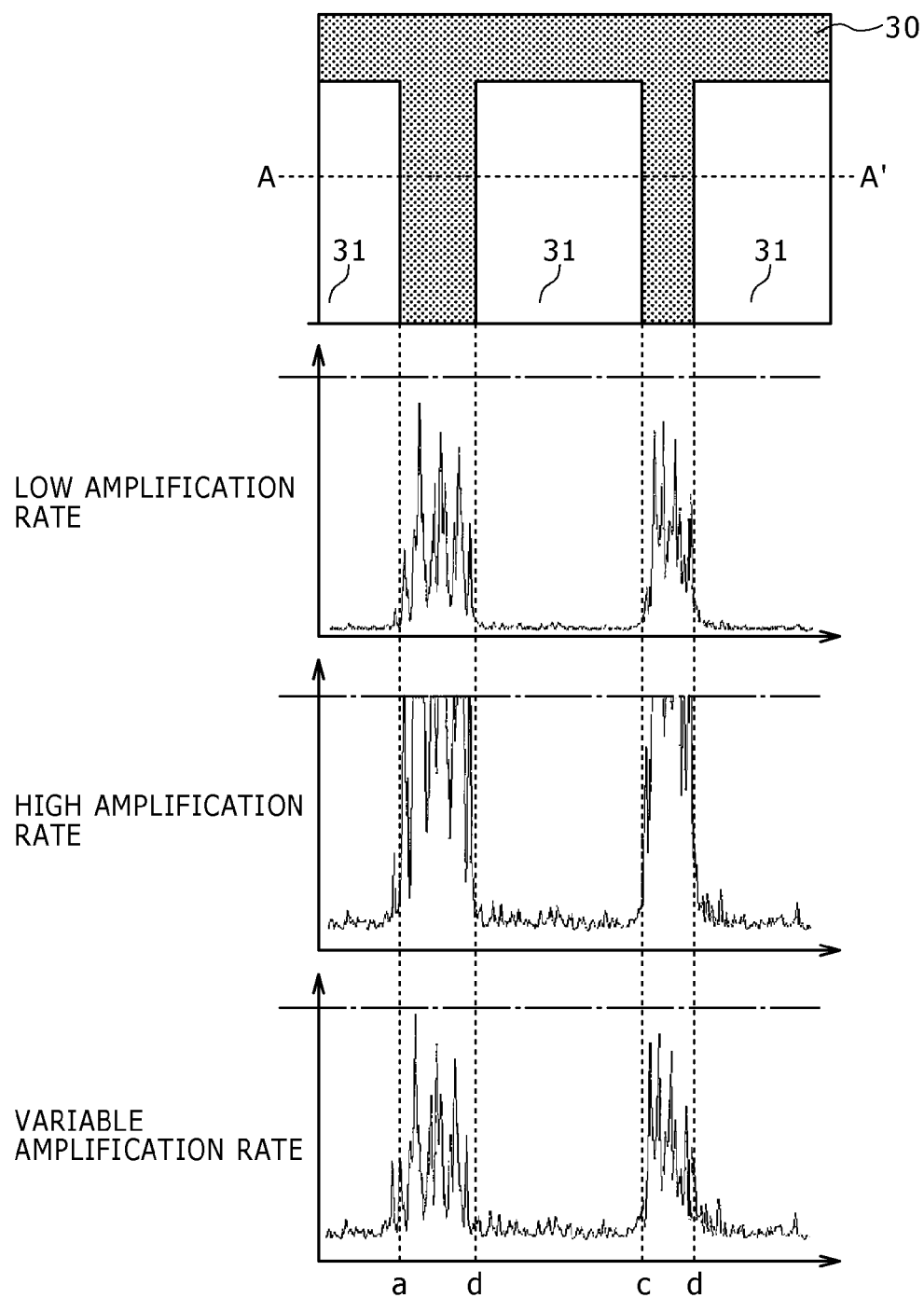
FIG. 6 is a diagram showing a difference in an image by an amplification rate of a sensor array according to the first embodiment of the present invention.
Figure 7:
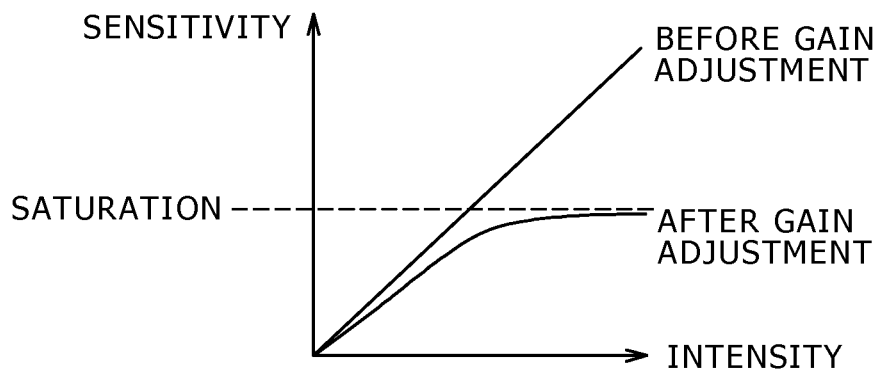
FIG. 7 is a diagram showing an amplification rate adjustment result of the sensor array according to the first embodiment of the present invention.

By using an amplification rate control function by a voltage of the sensor array 126, a dynamic range of the sensor can be expanded. FIG. 6 is a diagram showing a difference in image by an amplification rate of the sensor array according to the first embodiment of the present invention, and FIG. 7 is a diagram showing an amplification rate adjustment result of the sensor array according to the first embodiment of the present invention. FIG. 6 shows a relationship between an image profile acquired by the inspection and a sensor amplification rate. In an obtained image, there is an area (a bright section) 30 where a scattered light intensity that reaches to the sensor array 126 is strong and a weak area (a dark section) 31 where it is weak, partly due to an effect of insertion of a spatial filter. When an area 30 where the scattered light intensity is strong is acquired by lowering the amplification rate, the intensity is weak in the area 30 where the scattered light intensity is weak and there is a possibility of overlooking a defect. On the other hand, when the sensitivity of an area 31 where the scattered light intensity is low is raised by increasing the amplification rate, the signal goes to be saturated in the area 30 where the scattered light intensity is strong, which will make defect inspection impossible. Therefore, by setting the amplification rate low in the area 30 where the scattered light intensity is strong and by setting the amplification rate high in the area 31 where the scattered light intensity is weak, it is made possible to perform inspection with a widened dynamic range. That is, the image is acquired by dynamically changing a relationship between the scattered light intensity and the sensor amplification rate while the sensor amplification rate is being scanned so that the intensity may not reach the sensor saturation intensity as shown in FIG. 7.

Figure 8:
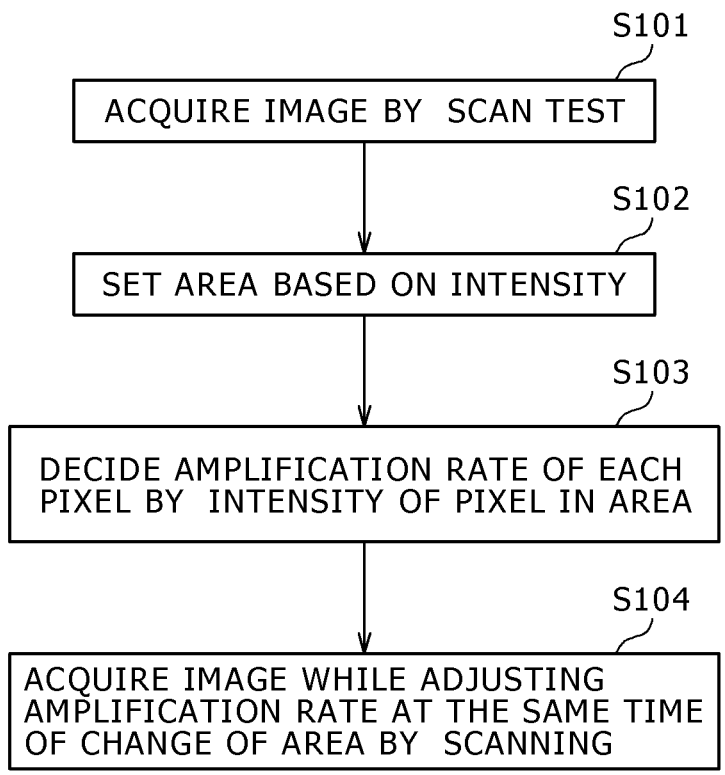
FIG. 8 is a flowchart of deciding of the amplification rate according to the first embodiment of the present invention.

A setting method of the sensor amplification rate will be explained in detail. If the amplification rate is made variable according to a detection intensity of only each pixel, there will be a possibility that a defect signal with high intensity may be detected with a low amplification rate and the sensitivity may fall. Therefore, the amplification rate is set for the bright section 30 and for the dark section 31, respectively, namely for each area where the scattered light intensity is the same, and the inspection is performed. FIG. 8 is a flowchart of deciding of the amplification rate according to the first embodiment of the present invention. Before the inspection, in order to decide conditions of the polarization generation part 114, the spatial filter 123, and the polarization analysis part 124, the inspection object is subjected to a scan test (S101). A boundary of the bright section and the dark section in a scanned image under inspection conditions obtained at that time is found and a setting area of the amplification rate is decided. Here, the boundary of the bright section and the dark section is found by carrying out statistical processing on brightness information in the image (S102). For example, this can be done by using a fact that variance is small in a place where brightness difference of the image is small, and the brightness difference is large and the variance becomes large near the boundary, that is, the area is set up by calculating a variance value of a fixed area over the entire image and determining a boundary value of the bright section and the dark section based on a magnitude of the variance. Next, an inspection scan is performed, and in each area set in S102, the amplification rate at the time of detecting the area is decided based on the intensity of the specified number of pixels acquired first in that area (S103). The amplification rate is decided as follows: a relationship between the detection intensity and the amplification rate has been decided first; an average intensity of first n pixels that are scanned in a certain area; and when the intensity is saturated, the amplification rate is reduced, and when the intensity is less than or equal to a fixed intensity, the amplification rate is increased so that the detection intensity may become suitable. This is performed repeatedly while being scanned (S104). By keeping setting the amplification rate in real time, a suitable amplification rate can be set in almost the entire area of the inspection object except near the boundary. When the same patterns exist in multiple places like a semiconductor pattern, the amplification rate decided in a first pattern may be applied to the same patterns. Moreover, at the time of setting the area, the setting may be done in advance using design data.

Figure 9:
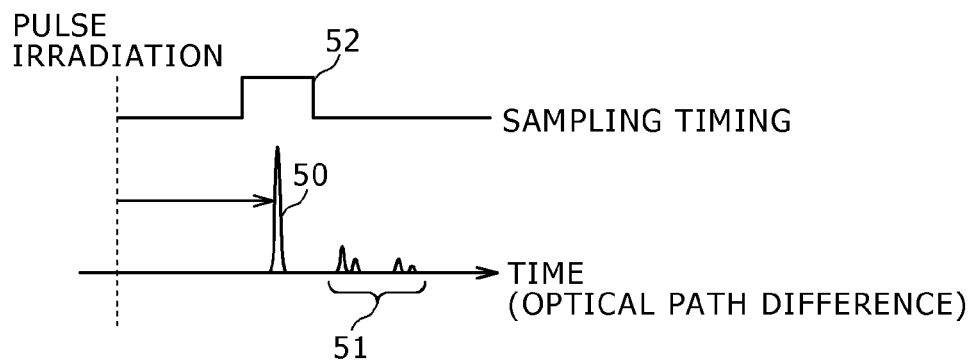
FIG. 9 is a diagram showing gate mode sampling by an oblique illumination system according to the first embodiment of the present invention.
Figure 10:
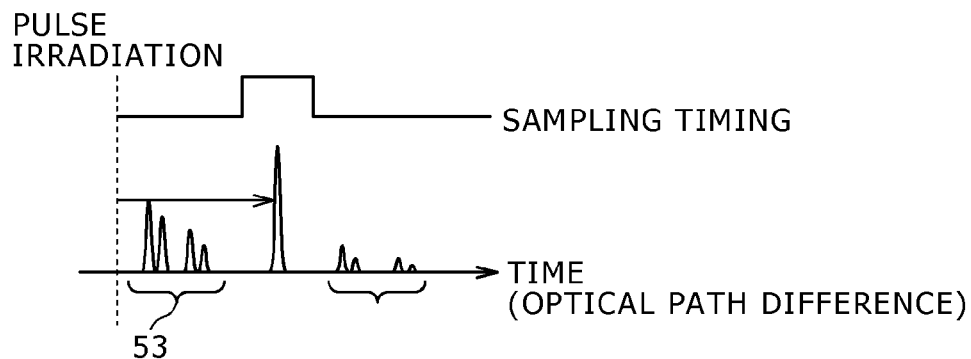
FIG. 10 is a diagram showing gate mode sampling by an epi-illumination system according to the first embodiment of the present invention.

When detecting the weak scattered light from the defect, the reflected light etc. occurring at each optical element becomes stray light, and the scattered light from the defect will be buried therein. It is possible to reduce this stray light by using the pulsed light source for the laser light source and making the sensor array 126 perform a high-speed response of switching ON/OFF of the detection within a time shorter than a pulse interval of the pulsed light source 111. This can be done just by using a gate mode of detecting light only at a timing when the scattered light from the defect by the pulsed illumination light reaches the sensor array 126 and its adjacent times. FIG. 9 and FIG. 10 are diagrams showing gate mode sampling by the oblique illumination system according to the first embodiment of the present invention. Stray light removal by combining the oblique illuminating optical system 110a and the gate mode of the sensor array 126 will be explained using FIG. 9. A time (an optical path difference) required for the pulse generated by the laser light source 111 to reach the sensor array 126 through the inspection object from the generation can be easily calculated with thicknesses of the optical elements, refractive indices, and a propagating distance in air. In the oblique illuminating optical system 110a, weak reflected light occurring in each optical element also irradiates the inspection object. Moreover, also when the scattered light from the inspection object propagates inside the detecting optical system 120, reflected light occurs at each optical element, and scattered light other than the direct scattered light from the inspection object reaches the sensor array and becomes stray light 51 there. Then, since a time for the scattered light from the inspection object that should be detected to reach the sensor array 126 is known, the stray light 51 can be removed by performing sampling just before and after a timing when it reaches (ideally, only direct scattered light 50 from the inspection object). Pieces of the stray light resulting from these optical elements cause sensitivity lowering more in the case of the epi-illuminating optical system 110b. Although the epi-illuminating optical system 110b uses a TTL (Through The Lens) system that makes the epi-illumination system and an upper detecting optical system coexist by using a detection lens of the detecting optical system also at the time of illumination, the use of the TTL system becomes a factor of large sensitivity lowering because reflected light 53 arising when the input light whose light quantity is large as compared with the scattered light of the inspection object passes through the detection lens reaches the sensor array 126 as shown in FIG. 10. Regarding the signal based on the scattered light detected in this way, an analog signal outputted from the sensor array 126 is amplified by the A/D conversion part 129, and subsequently is converted into a digital signal, which is sent to the signal processing and control part 250, where the signal is processed.

[Stage Part 170]

The stage part 170 is comprised by having an x-stage 170a, a y-stage 170b, a z-stage 170c, and a θ-stage 170d. The x-stage 170a is a stage that is movable in an x direction and mounts thereon a semiconductor wafer 100 that is a sample to be inspected and on whose surface a minute pattern is formed. The y-stage 170b, the z-stage 170c, and the θ-stage 170d are also stages similarly movable in the y direction, a z direction, and a θ direction, respectively, that mounts thereon the semiconductor wafer 100 that is the sample to be inspected and on whose surface a minute pattern is formed.

[Reflected Light Analysis Part 300]

In the image obtained by the detecting optical system 120, its intensity is governed by interference of a thin film on a surface of the inspection object. Therefore, existence of film thickness unevenness makes unevenness in the brightness of the obtained image occur. Although it will be described later, defect detection is performed based on a difference of brightness between a normal section and a defect section by die comparison of the inspection object, there is a case where performance of the defect detection may lower if there exists unevenness in brightness over the whole of the image. Therefore, a reflected light analysis part 300 analyzes direct reflected light from the inspection object under the illumination light by the oblique illuminating optical system 110a to estimate a film thickness of the thin film, and compensates brightness unevenness resulting from the film thickness unevenness of the image that is detected by the detecting optical system 120.

Figure 11:
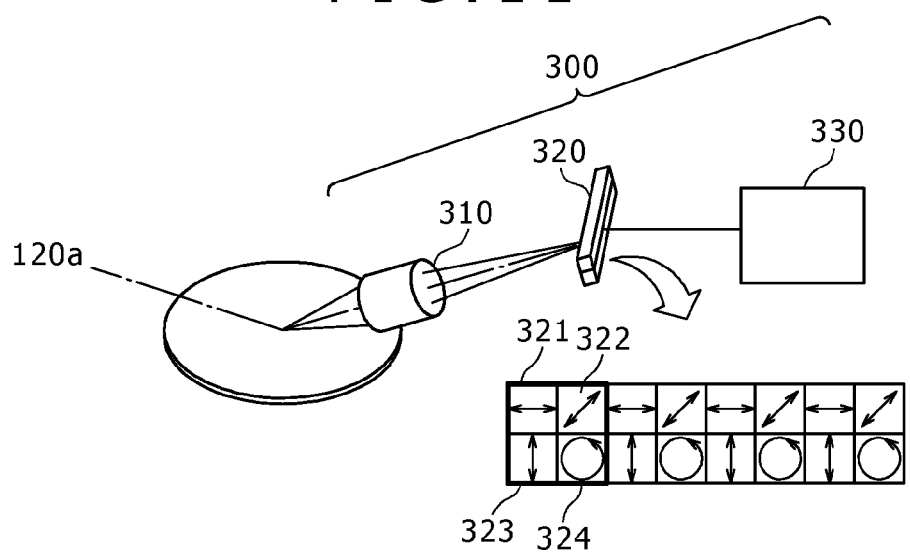
FIG. 11 is a diagram showing a film thickness analysis part according to the first embodiment of the present invention.

FIG. 11 is a diagram showing a film thickness analysis part according to the first embodiment of the present invention. FIG. 11 explains details of compensation of the brightness unevenness. The direct reflected light from the oblique illuminating optical system 110a is imaged on a sensor 320 with a lens 310. Either of a micro linear polarizer or a micro circular polarizer is disposed in front of each pixel of the sensor 320. The film thickness is estimated by a film thickness estimation part 330 using a technique of the ellipsometry that is a general method of film thickness analysis, i.e., by specifying four combinations of micro linear polarizers 321 to 323 and a micro circular polarizer 324 that are different in an azimuth of transmission axis as one group and detecting polarized lights of multiple states using a range defined by these four pixels as a spatial resolution. A difference in a scattered light quantity by a film thickness variation can be assumed by an optical simulation provided that a structure of the inspection object is known, and this corresponds to the brightness unevenness of an image. The brightness unevenness of the image obtained here is compensated before performing image processing. Alternatively, the brightness unevenness may be fed back to the amplification rate of the sensor array 126 to directly acquire an image whose brightness unevenness is compensated.

When using the epi-illuminating optical system 110b, the branching mirror 116 is specified to be a beam splitter through which regular reflected light can pass by an amount that enables the detection, and the brightness unevenness is reduced similarly with the oblique illuminating optical system 110a. In this occasion, although the scattered light of the oblique illuminating optical system 110a also reaches the sensor array 126, its detection is avoided by the gate mode sampling of the sensor array 126.

[Signal Processing and Control Part 250]

The signal processing and control part 250 is comprised by having an image processing part 200, an operation part 210, a control part 220, a display part 230, and a height detecting part 160. Concrete examples of a signal processing part are shown in FIG. 12 to FIG. 15.

Figure 12:
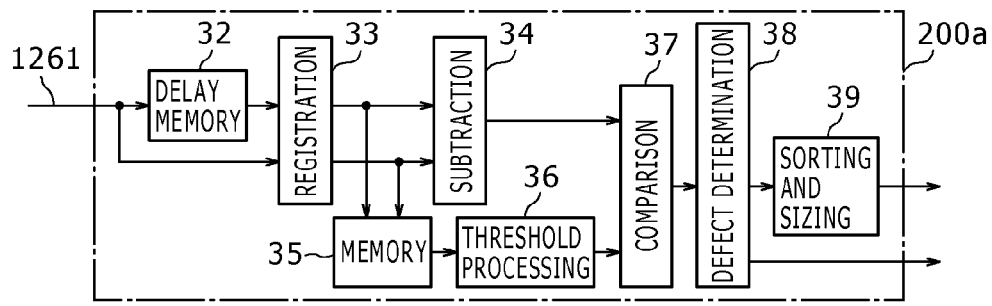
FIG. 12 is a block diagram showing an image processing configuration according to the first embodiment of the present invention.

FIGS. 12 to 15 are block diagrams each showing an image processing configuration according to the first embodiment of the present invention. Processing of a signal processing part 200a shown in FIG. 12 is generally known as die comparison processing. That is, an image of a certain die has been memorized in delay memory 32, when an image of an adjacent die is acquired, the registration is performed by a registration circuit 33 in order to correct positional shift resulting from vibration etc., and an acquired image is subtraction processed by a subtraction circuit 34. In parallel with this, the image that was subjected to the registration is memorized in memory 35, and a threshold is calculated by a threshold processing circuit 36. The signal that was subjected to the above-mentioned subtraction processing and the threshold are subjected to the comparison processing in a comparator circuit 37, and a foreign substance signal and the defect signal are extracted by a defect determination part 38. The extracted foreign substance and defect signals are outputted, as it is, as a defect map, or are sorted for each of foreign substance kinds and defect kinds by a sorting and sizing processing part 39, whereby sizes of the foreign substances and the defects are found.

Figure 13:
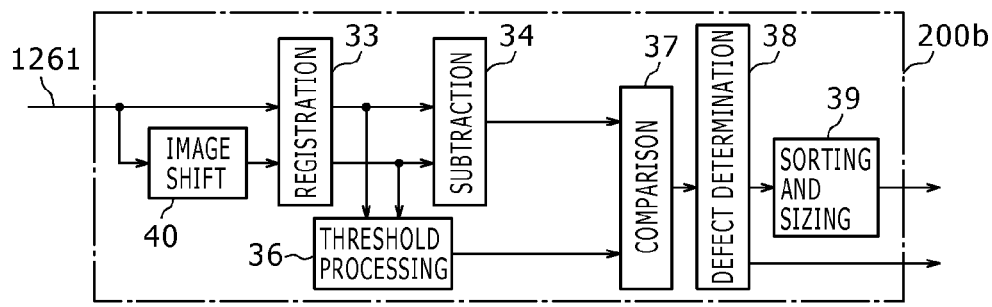
FIG. 13 is a block diagram showing an image processing configuration according to the first embodiment of the present invention.

Processing of a signal processing part 200b shown in FIG. 13 is generally known as cell comparison processing. That is, when the obtained image includes a signal from a pattern that is originally in an identical shape, the image is shifted by an image shift circuit 40, in order to take a corresponding point between the image before the shift and the image after the shift, the registration is performed by the registration circuit 33, and the obtained image is subtraction processed by the subtraction circuit 34. In parallel with this, the image that was subjected to the registration is memorized in the memory 35, and a threshold is calculated by the threshold processing circuit 36. The signal that was subjected to the above-mentioned subtraction processing and the threshold are subjected to the comparison processing and the foreign substance signal and the defect signal are extracted by the defect determination part 38. The extracted foreign substance and defect signals are outputted, as it is, as a defect map, or are sorted for each of the foreign substance kinds and the defect kinds by the sorting and sizing processing part 39, whereby the sizes of the foreign substances and the defects are found.

Figure 14:
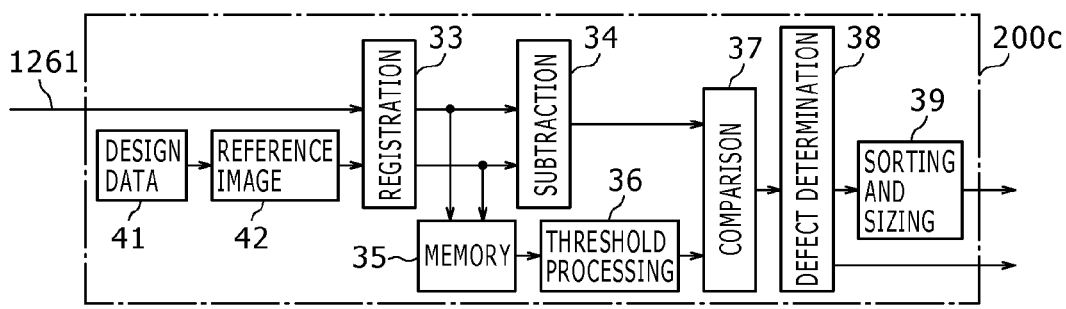
FIG. 14 is a block diagram showing an image processing configuration according to the first embodiment of the present invention.

Processing of a signal processing part 200c shown in FIG. 14 is generally known as design data comparison processing. That is, the design data from design data 41 is sent to a reference image generation part 42, where the reference image is generated. The reference image is subjected to registration in order to take corresponding points with an actual image and the obtained image is subtraction processed in the subtraction circuit 34. In parallel to this, the image that was registered is memorized in the memory 35, and a threshold is calculated by the threshold processing circuit 36. The signal that was subjected to the above-mentioned subtraction processing and the threshold are subjected to the comparison processing in the comparator circuit 37, and the foreign substance signal and the defect signal are extracted by the defect determination part 38. The extracted foreign substance and defect signals are outputted, as it is, as a defect map, or are sorted for each of the foreign substance kinds and the defect kinds by the sorting and sizing processing part 39, whereby the sizes of the foreign substances and the defects are found.

Figure 15:
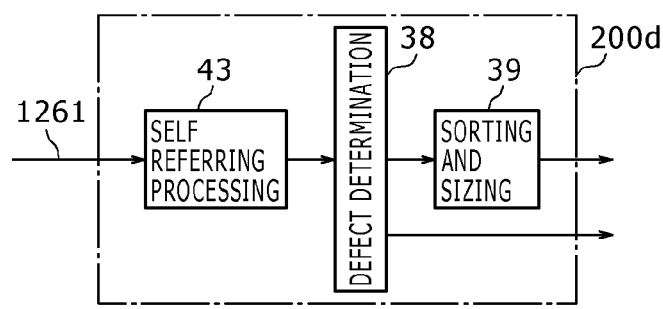
FIG. 15 is a block diagram showing an image processing configuration according to the first embodiment of the present invention.

A system of a signal processing part 200d shown in FIG. 15 is generally known as a self referencing system. That is, the signal processing part 200d carries out defect determination by searching a similar pattern in the obtained image and performing the comparison processing on the similar patterns, and determines a defect based on feature quantities of the pattern and the defect. In addition to this, although it is not illustrated, a processing system that forms an image from an average value of multiple similar patterns and performs the comparison processing using the image as the reference image is also known.

Second Embodiment

Figure 16:
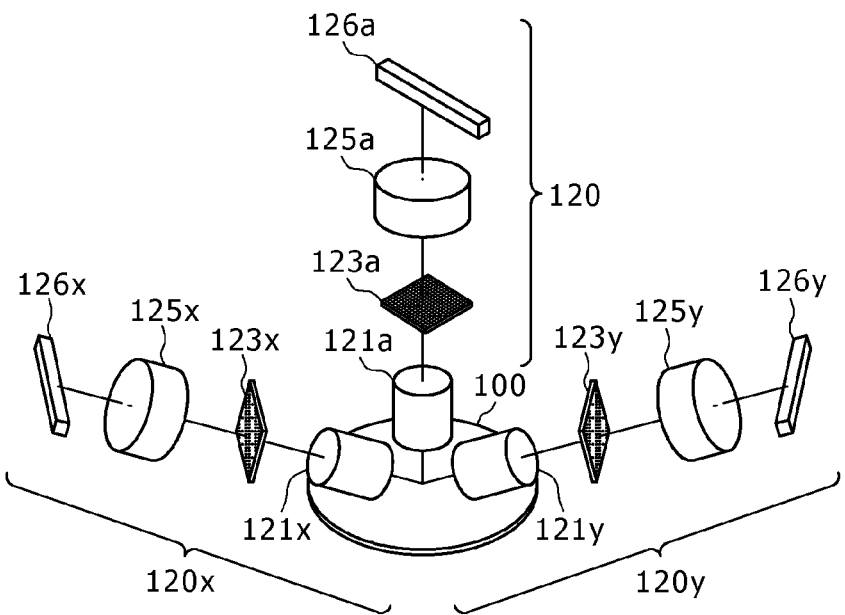
FIG. 16 is a block diagram showing a detector configuration of an optical inspecting apparatus according to a second embodiment of the present invention.
Figure 17:
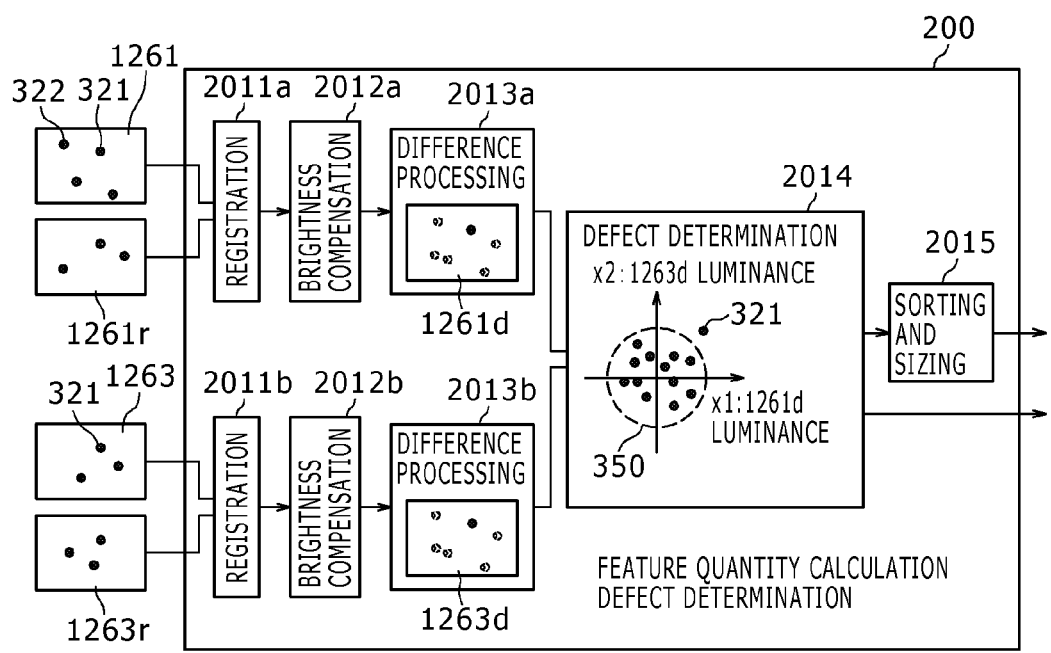
FIG. 17 is a block diagram showing an image processing configuration according to the second embodiment of the present invention.

A second embodiment of the optical inspecting apparatus according to the present invention will be described using FIG. 16 and FIG. 17. FIG. 16 is a block diagram showing a detector configuration of an optical inspecting apparatus according to the second embodiment of the present invention, and FIG. 17 is a block diagram showing an image processing configuration according to the second embodiment of the present invention. Below, the dark field inspecting apparatus will be explained taking inspection of the dark field inspecting apparatus as an example.

Although the detecting optical system was single in the first embodiment, the optical system of the second embodiment has multiple detecting optical systems. FIG. 16 shows only the detecting optical system. The dark field inspecting apparatus has oblique detecting systems 120x, 120y in addition to the same upper detecting optical system 120 as that of the first embodiment. The configurations of the oblique detecting systems 120x, 120y are the same as that of the upper detecting optical system 120. However, since a common portion of the focal plane of the oblique detection lens and the inspection object becomes a linear shape, unless a width of a thin line of the illumination light is made thin to the same level as the focal depth of the detecting optical system, out-of-focus light will also be detected by the sensor array and an image with a high contrast cannot be obtained.

The scattered light of the defect differs in the scattered direction depending on its shape and a medium. Because of this, improvement in a capture ratio is expected by detecting the scattered light going in multiple azimuths with multiple detectors. Moreover, accuracies such as of defect sorting and sizing are improved by using a ratio of the defect signals acquired by the detectors. Below, the image processing part 200 at the time of acquiring two images will be explained in detail. The image processing part 200 generates an image 1261 based on the scattered light acquired by the detecting optical system 120 and a reference image 1261r acquired at a portion having the same shape as that of the acquisition place of the image 1261 in an adjacent die or cell; an image registration processing part 2011a performs registration on this generated image 1261 and the reference image 1261r with an accuracy less than or equal to a pixel unit of the sensor; a brightness compensation part 2012a compensates brightness of the inspection image 1261 and the reference image 1261r that arises from the sample such as a sample surface and a thickness of a thin film on the surface layer or arises from the optical system such as a difference of height between the lens and the wafer at the time of inspection; and a difference processing part 2013a performs difference processing whereby corresponding pixels of the inspection image 1261 and the reference image 1261r are subtracted from each other to obtain a difference image 1261d. In this case, the reference image 1261r generated based on the scattered light that was acquired by the detecting optical system 120 at a portion having the same shape as that of an acquisition place of the image 1261 in a die, a cell, or the like that is adjacent is temporarily memorized in an unillustrated image memory. The image registration processing part 2011a calls the reference image 1261r from the image memory, and performs registration processing with the image 1261 with an accuracy less than or equal to the pixel unit. Moreover, an image 1263 that contains a defect and a reference image 1263r are generated from a signal acquired from the detecting optical system 120x, and the processing is performed on this image 1263 and the reference image 1263r by the same configuration, which gives a difference image 1263d.

Next, in a defect determination part 2014, a rectangular coordinate system in which a luminance value of the difference image 1261d is represented on a horizontal axis x1 and a luminance value of the difference image 1263d is represented on a vertical axis x2 is configured and luminances of corresponding pixels of the two difference images 1261d and 1263d are plotted in this rectangular coordinate system x1, x2. Since noises are residuals of subtraction between a defect image and a reference image in an x1-x2 space of the rectangular coordinate system, both components x12, x2 are small and the noises are distributed near the origin. On the other hand, intensity of the brightness of the defect image is large as compared with noises, and the defect image is plotted so as to be located at a position away from the origin in the x1-x2 space. Then, by providing a boundary 350 near the origin of the rectangular coordinate system, a noise 322 and a defect 321 are separated and the defect determination is carried out (2014). A circle, a combination of lines, etc. are usable for the boundary 350. For example, when a circle is used, what is necessary is that a boundary line is drawn in an area that satisfies the following formula (Formula 1) with a radius of the circle set to A.

The following formula shall hold.

$$\sum_i x_i^2 = A^2 (i = 1, 2) \quad \text{[Formula 1]}$$

Although the example about the two images was shown here, the same processing can be also used even when using three or more images. From the features such as a scattered light distribution, the intensity, etc. of these extracted defect candidates, the defect determination and the sorting and sizing are carried out in a sorting and sizing processing part 2015.

What is claimed is:

1. A defect inspecting apparatus, comprising:
an illuminating optical system having a laser light source for irradiating a sample;
a detecting optical system having a sensor for detecting light generated from the sample; and
a signal processing unit that extracts a defect from an image generated from the light,
wherein an amplification rate of the sensor is set based on brightness information from a predetermined image, and
wherein the amplification rate is dynamically adjusted during a time the light is detected.

2. The defect inspecting apparatus according to claim 1, wherein the amplification rate is adjusted based on the light.

3. The defect inspecting apparatus according to either claim 1,
wherein the amplification rate is adjusted based on a magnitude of the light.

4. The defect inspecting apparatus according to claim 1,
wherein the amplification rate is adjusted for predetermined areas of the sample based on the brightness information.

5. The defect inspecting apparatus according to claim 1,
wherein the amplification rate is dynamically adjusted based on an intensity of light from a predetermined number of pixels of the sample.

6. The defect inspecting apparatus according to claim 1, wherein the sensor is an avalanche photodiode.

7. A defect inspecting apparatus, comprising:
an illuminating optical system having a laser light source for irradiating a sample on whose surface a pattern is formed with light;
a detecting optical system having a sensor for detecting light generated from the sample illuminated by the illuminating optical system; and
a signal processing unit that extracts a defect from an image based on the light detected by the detecting optical system,
wherein the laser light source is a pulsed light source,
wherein the sensor switches ON/OFF within a time shorter than a pulse interval of the pulsed light source, and
wherein an amplification rate of the sensor is dynamically changed during a time when the light is detected by the detecting optical system.

8. The defect inspecting apparatus according to claim 1,
wherein the laser light source is a pulsed light source, and
wherein the sensor performs sampling when a pulse of the pulsed light source reaches the sensor.

9. The defect inspecting apparatus according to claim 1,
wherein the detecting optical system comprises a plurality of sensors for detecting light scattered at different elevation angles with respect to a surface of the sample, and
wherein the signal processing unit performs integrated processing on the light, respectively.

10. An defect inspecting method, comprising:
irradiating a sample;
detecting light generated from the sample; and
extracting a defect from an image generated from the light,
wherein an amplification of a sensor is set based on brightness information from a predetermined image, and
wherein the amplification rate is dynamically adjusted during a time the light is detected.

11. The defect inspecting method according to claim 10,
wherein the amplification rate is adjusted based on the light.

12. The defect inspecting method according to claim 10,
wherein the amplification rate is adjusted based on a magnitude of the light.

13. The defect inspecting method according to claim 10,
wherein the amplification rate is adjusted for every predetermined areas of the sample based on the brightness information.

14. The defect inspecting method according to claim 10,
wherein the amplification rate is dynamically adjusted based on an intensity of light from a predetermined number of pixels of the sample.

15. The defect inspecting method according to claim 10,
wherein the sensor is an avalanche photodiode.

16. The defect inspecting method according to claim 10
wherein irradiating the sample is by a pulsed light source, and
wherein the sensor performs sampling when a pulse of the pulsed light source reaches the sensor.

17. The defect inspecting method according to claim 10,
wherein detecting light scattered at different elevation angles with respect to a surface of the sample, respectively, and
wherein integrated processing is performed on the scattered light.

18. The defect inspecting apparatus according to claim 1,
wherein the laser light source is a pulsed light source, and
wherein the sensor switches ON/OFF within a time shorter than a pulse interval of the pulsed light source.

19. The defect inspecting method according to claim 10,
wherein irradiating the sample by a pulsed light source, and
wherein the sensor switches ON/OFF within a time shorter than a pulse interval of the pulsed light source.

* * * * *